(12) United States Patent
Dahl et al.

(10) Patent No.: US 9,365,896 B2
(45) Date of Patent: Jun. 14, 2016

(54) ADDITION OF AN ADAPTOR BY INVASIVE CLEAVAGE

(71) Applicant: Agilent Technologies, Inc., Loveland, CO (US)

(72) Inventors: Fredrik Dahl, Sigtuna (SE); Olof John Ericsson, Uppsala (SE); Henrik Johansson, Uppsala (SE); Maithreyan Srinivasan, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 112 days.

(21) Appl. No.: 13/963,723

(22) Filed: Aug. 9, 2013

(65) Prior Publication Data

US 2014/0113296 A1    Apr. 24, 2014

Related U.S. Application Data

(60) Provisional application No. 61/715,980, filed on Oct. 19, 2012.

(51) Int. Cl.
 *C12Q 1/68* (2006.01)
(52) U.S. Cl.
 CPC ............ *C12Q 1/6855* (2013.01); *C12Q 1/6806* (2013.01); *C12Q 2525/101* (2013.01); *C12Q 2525/179* (2013.01)
(58) Field of Classification Search
 None
 See application file for complete search history.

(56) References Cited

U.S. PATENT DOCUMENTS

| 7,883,849 | B1 | 2/2011 | Dahl | |
| 2005/0142577 | A1* | 6/2005 | Jones et al. | 435/6 |
| 2006/0008824 | A1* | 1/2006 | Ronaghi et al. | 435/6 |
| 2009/0061424 | A1* | 3/2009 | Chen | 435/6 |
| 2009/0176234 | A1 | 7/2009 | Drmanac et al. | |
| 2009/0176652 | A1 | 7/2009 | Dahl et al. | |
| 2009/0203551 | A1 | 8/2009 | Dahl et al. | |
| 2011/0281736 | A1 | 11/2011 | Drmanac et al. | |
| 2012/0100534 | A1 | 4/2012 | Drmanac et al. | |
| 2012/0122699 | A1 | 5/2012 | Dahl et al. | |

OTHER PUBLICATIONS

Odell et al. Virology (1996) 221: 120-129.*
Dahl, et al. "Multiplex amplification enabled by selective circularization of large sets of genomic DNA fragments", Nucleic Acids Research, 2005, vol. 33, No. 8, e71 (7 pages).

* cited by examiner

*Primary Examiner* — Angela M Bertagna (57) ABSTRACT

This disclosure provides a method for adding an adaptor to a genomic sequence by invasive cleavage, as well as a kit for performing the method. In some embodiments, the method comprises: a) hybridizing genomic DNA to an adaptor comprising a double stranded region and a single stranded region comprising a 5' overhang to produce a substrate for a flap endonuclease; b) cleaving the substrate using the flap endonuclease; c) ligating the recessed end of the double stranded region to the fragment to produce an adaptor-ligated DNA; d) intramolecularly ligating the ends of the adaptor-ligated DNA to produce a circular DNA molecule; and e) enzymatically processing the circular DNA molecule using an oligonucleotide that hybridizes to the adaptor and an enzyme. A kit for performing the method is also provided.

18 Claims, 2 Drawing Sheets

ADDITION OF AN ADAPTOR BY INVASIVE CLEAVAGE

BACKGROUND

Several analytical methods in molecular biology (e.g., sequencing library preparation) require that an adaptor is placed onto the end of a DNA fragment in order to provide a way to manipulate that fragment. For example, one or more adaptors may be ligated onto a fragment of DNA to produce an adaptor-ligated fragment, and the adaptor-ligated fragment may be amplified and/or sequenced using a primer binding site that is present in the added adaptor.

SUMMARY

Provided herein is a method comprising: a) hybridizing genomic DNA to an adaptor, wherein the adaptor comprises: a double stranded region, a single stranded region comprising a 5' overhang and a nucleotide sequence for subsequent enzymatic processing; wherein the 5' overhang hybridizes to the genomic DNA to produce a substrate for a flap endonuclease; b) cleaving the substrate using the flap endonuclease to produce a product comprising the adaptor and a flap endonuclease-generated fragment of the genomic DNA that is hybridized to the 5' overhang and ligatable to the recessed end of the double stranded region; c) ligating the recessed end of the double stranded region to the fragment to produce an adaptor-ligated DNA; d) intramolecularly ligating the ends of the adaptor-ligated DNA to produce a circular DNA molecule; and e) enzymatically processing the circular DNA molecule using an oligonucleotide that hybridizes to the adaptor and an enzyme. In certain cases, the double stranded region of the adaptor may contain binding sites for inverse PCR primers, for amplification PCR. In these embodiments, the enzymatic processing may comprise amplifying the circular DNA molecule using PCR with primers that bind to those sites. The amplified product may be sequenced. A kit for performing the method is also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" also refers to "a biological sample." As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "biological sample" can also refer to cells or tissue analyzed in vivo, i.e., without removal from animal. Typically, a "biological sample" will contain cells from the animal, but the term can also refer to non-cellular biological material, such as non-cellular fractions of blood, saliva, or urine, that can be used to measure the cancer-associated polynucleotide or polypeptides levels. "A biological sample" further refers to a medium, such as a nutrient broth or gel in which an organism has been propagated, which contains cellular components, such as proteins or nucleic acid molecules.

The term "nucleic acid sample," as used herein denotes a sample containing nucleic acids. A nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "partitioning", with respect to a genome, refers to the separation of one part of the genome from the remainder of the genome to produce a product that is isolated from the remainder of the genome. The term "partitioning" encompasses enriching.

The term "genomic region", as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "genomic sequence", as used herein, refers to a sequence that occurs in a genome.

The term "genomic fragment", as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment), or non-adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "affinity tag", as used herein, refers to moiety that can be used to separate a molecule to which the affinity tag is attached from other molecules that do not contain the affinity tag. An "affinity tag" is a member of a specific binding pair, i.e. two molecules where one of the molecules through chemical or physical means specifically binds to the other molecule. The complementary member of the specific binding pair, referred to herein as a "capture agent" may be immobilized (e.g., to a chromatography support, a bead or a planar surface) to produce an affinity chromatography support that specifically binds the affinity tag. In other words, an "affinity tag" may bind to a "capture agent", where the affinity tag specifically binds to the capture agent, thereby facilitating the separation of the molecule to which the affinity tag is attached from other molecules that do not contain the affinity tag.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

The term "terminal nucleotide", as used herein, refers to the nucleotide at either the 5' or the 3' end of a nucleic acid molecule. The nucleic acid molecule may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

A "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "separating", as used herein, refers to physical separation of two elements (e.g., by size or affinity, etc.) as well as degradation of one element, leaving the other intact.

The term "target sequence" refers to a sequence that is in an unmodified genome, as well as genomes that have been modified (e.g., fragmented and/or adaptor-ligated) or copied. An oligonucleotide that hybridizes to a target genomic sequence base-pairs with the genome sequence. A genomic fragment that contains a target sequence may be in the range of 0.5 kb in length to over 500 kb in length or more, e.g., 5 kb to 100 kb, for example.

The term "reference chromosomal region," as used herein refers to a chromosomal region of known nucleotide sequence, e.g. a chromosomal region whose sequence is deposited at NCBI's Genbank database or other database, for example.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

As used herein, the term "label" refers to any atom or molecule that can be used to provide a detectable (preferably quantifiable) effect, and that can be attached to a nucleic acid or protein. Labels include but are not limited to dyes and radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable. The term "labeled dNTPs" refers to the dNTPs that are modified by the attached labels. The term "labeled ddNTPs" refers to the ddNTPs that are modified by the attached labels.

The term "labeled oligonucleotide", as used herein, refers to an oligonucleotide that is has an affinity tag (e.g., a biotin moiety) an oligonucleotide modified with atoms or groups enabling separation or detection (e.g., bromo-deoxyuridine, or colloidal gold particles conferring different density), an oligonucleotide modified with or an optically detectable label (e.g., a fluorescence or another type of light emitting label). Oligonucleotides that contain only naturally occurring nucleotides are not labeled oligonucleotides.

The term "adaptor" refers to double stranded adaptors, single stranded adaptors, and adaptors that are partially double stranded and partially single stranded. An adaptor can be DNA or RNA, or can contain both DNA and RNA.

The term "surface-tethered" refers to a molecule that is immobilized on a surface of a solid substrate, where the substrate can have a variety of configurations, e.g., a sheet, bead, or other structure.

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "enzymatic processing" refers to a covalent modification that is catalyzed by an enzyme (e.g., a polymerase or restriction enzyme, for example). Primer extension (including PCR, rolling circle amplification), transcribing (e.g., using, e.g., T7 or T3 polymerase) and digesting (e.g., using a restriction enzyme) are all types of enzymatic processing).

The term "subsequent enzymatic processing" refers to enzymatic processing step that occurs later in a protocol.

The term "extending", as used herein, refers to the extension of a primer by the addition of nucleotides using a polymerase. If a primer that is annealed to a nucleic acid is extended, the nucleic acid acts as a template for extension reaction.

The term "clonal PCR" is a PCR technique in which each reaction is done on a single template molecule, and the PCR reactions are kept spatially separated from one another. Bridge PCR and emulsion PCR, commonly used in next generation sequencing applications, are examples of clonal PCR.

The term "bridge PCR" refers to a solid-phase polymerase chain reaction in which the primers that are extended in the reaction are tethered to a substrate by their 5' ends. During amplification, the amplicons form a bridge between the tethered primers. Bridge PCR (which may also be referred to as "cluster PCR") is used in Illumina's Solexa platform. Bridge PCR and Illumina's Solexa platform are generally described in a variety of publications, e.g., Gudmundsson et al (Nat. Genet. 2009 41:1122-6), Out et al (Hum. Mutat. 2009 30:1703-12) and Turner (Nat. Methods 2009 6:315-6), U.S. Pat. No. 7,115,400, and publication application publication nos. US20080160580 and US20080286795. Bridge PCR is a type of "clonal PCR", i.e., is a PCR technique in which each reaction is begun on a single template molecule, and the PCR reactions are kept spatially separated from one another.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of a oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

As used herein, the term "flap cleavage reaction" refers to a reaction in which a substrate is cleaved in an overlap-dependent manner by a flap endonuclease to release a flap. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447).

The term "inverse PCR primers" as used herein refers to a pair of primers that point away from one another when they are annealed to double stranded DNA.

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

The term, "intramolecularly ligating" refers to a ligation in which the 5' end and the 3' end of a strand of nucleic acid are ligated to one another to produce a circular DNA molecule.

Other definitions of terms may appear throughout the specification.

DESCRIPTION OF EXEMPLARY EMBODIMENTS

This disclosure provides a method for adding an adaptor to a genomic sequence by invasive cleavage, as well as a kit for performing the method. In certain embodiments, the method may be used to produce a library of randomly generated genomic fragments that each contain the adaptor sequence ligated thereto. These embodiments have particular application in whole genome sequencing. In other embodiments, the method may be used to produce a library of target genomic fragments that each contain the adaptor sequence ligated thereto. These embodiments have particular application in targeted re-sequencing applications and mapping of SNPs, for example.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 1:
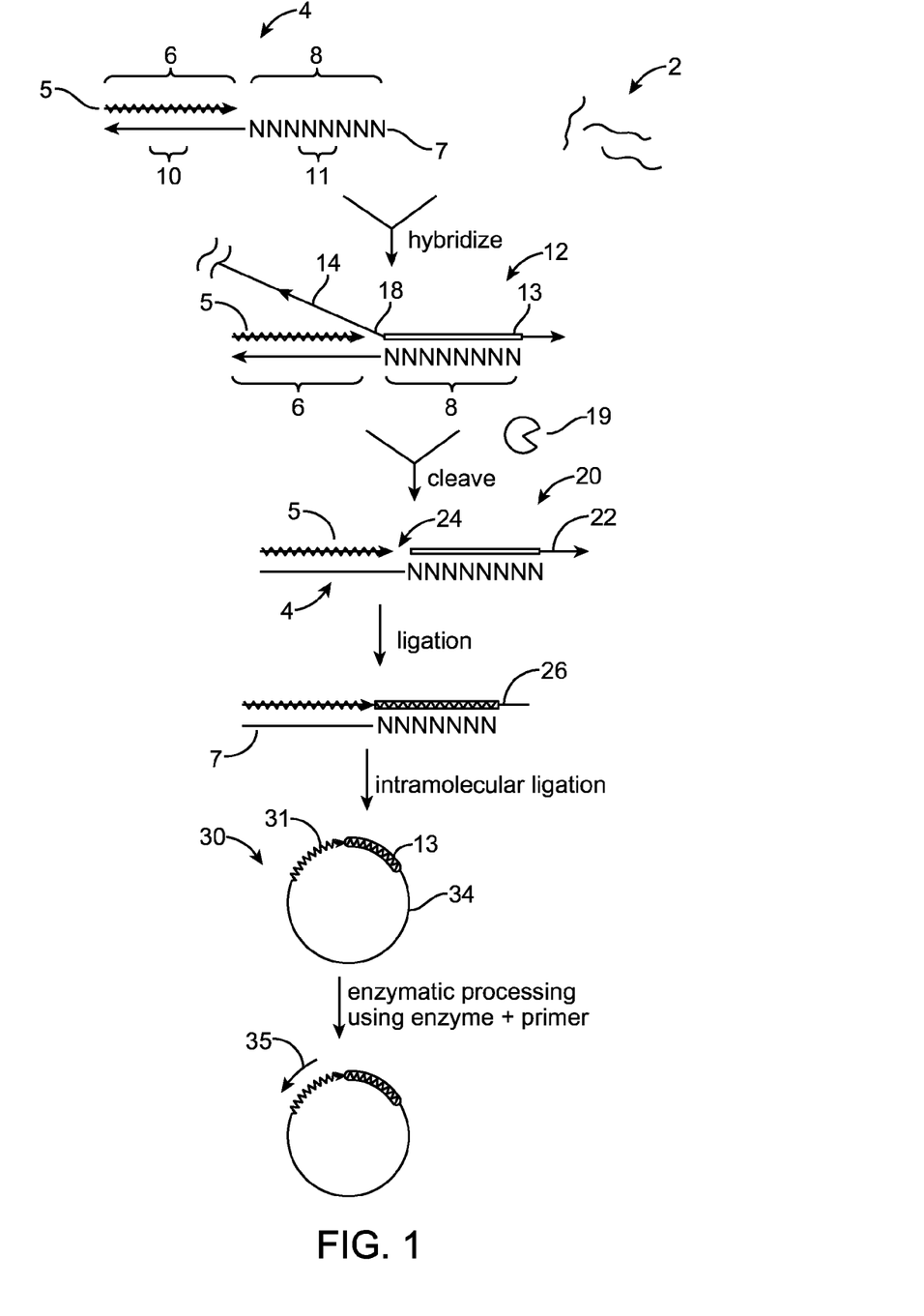
FIG. 1 schematically illustrates one embodiment of the subject method.

With reference to FIG. 1, certain embodiments of the method comprise hybridizing genomic DNA 2 to adaptor 4. As shown, adaptor 4 comprises double stranded region 6, single stranded region 8 that comprises a 5' overhang, and a nucleotide sequence for subsequent enzymatic processing (indicated by 10 and 11; this sequence can be in double stranded region 6 or single stranded region 8). The shorter oligonucleotide of the adaptor (referred to herein as the "recessed oligonucleotide") is indicated as element 5. The "recessed end" of the adaptor is the 3' end of the recessed oligonucleotide. The longer oligonucleotide of the adaptor (referred to herein as the "overhang oligonucleotide" is indicated as element 7. As shown, the nucleotide sequence for subsequent enzymatic processing may be present in double stranded region 6 (indicated by element 10) and/or in single stranded region 8 (indicated by element 11). The single stranded region is composed of a series of nucleotides, "N's", that hybridize to the genomic DNA. The double stranded region is designed so that it does not hybridize with the genomic DNA or to the single stranded region. As will be described in greater detail below, single stranded region 8 may contain a degenerate sequence and/or a sequence of nucleotide analogs that base pairs with any nucleotide. In these embodiments, the single stranded region may hybridize to randomly positioned sites in the genomic DNA. In alternative embodiments, the single stranded region may contain a specific, defined, sequence that hybridizes to a target site in the genomic DNA. In these embodiments, the single stranded region may hybridize to defined positions in the genomic DNA. Upon hybridization of genomic DNA 2 to adaptor 4, single stranded region 8 of adaptor 4 hybridizes to the genomic DNA to produce flap endonuclease substrate 12, i.e., a complex that comprises three distinct molecules and contains an overlapping sequence that is cleavable by a flap endonuclease. As shown, single stranded region 8 of adaptor 4 hybridizes to a site in the genomic DNA (13), and the nucleic acid that is 5' to that site (indicated by element 14) is displaced by recessed oligonucleotide 5. This hybridization (in which recessed oligonucleotide 5 effectively acts as an invasive oligonucleotide) results in the production of an overlapping nucleotide 18 that is cleaved by flap endonuclease. Cleavage of substrate 12 using flap endonuclease 19 produces product 20 that contains adaptor 4 and flap endonuclease-generated fragment 22 of genomic DNA. As shown in FIG. 1, after cleavage, flap endonuclease-generated fragment 22 remains hybridized to the single stranded overhang of the adaptor. This product contains a ligatable junction 24 in which the 3' end of recessed oligonucleotide 5 is ligatably adjacent to the 5' end of the flap endonuclease-generated fragment 22. Fragment 22 contains binding site 13 and sequence 3' to that binding site. Next, the recessed end the double stranded region is ligated (using, e.g., a double stranded ligase such as T4 ligase) to endonuclease-generated fragment 22 to produce an adaptor-ligated DNA 26. As shown, this product is hybridized to overhang oligonucleotide 7. After denaturing the duplex to remove overhang oligonucleotide 7, the ends of adaptor-ligated DNA 26 may be intramolecularly ligated to produce circular DNA molecule 30. This step may be done using a single stranded DNA ligase in certain embodiments. As indicated, circular DNA molecule 30 contains: sequence 31 that is the same as that of recessed oligonucleotide 5, sequence 13 (which sequence hybridized with single stranded region 8); and genomic sequence 34 (which lies 3' to binding site 13).

After circular DNA molecule 30 has been produced it is enzymatically processed, i.e., processed using an enzyme in the presence of oligonucleotide 35 that hybridizes to the sequence of recessed oligonucleotide 5. The enzymatical processing may comprise primer extension, sequencing, amplification, and/or enzymatic cleavage and the like. As noted above, the enzymatic processing may involve extending a primer that is hybridized to the adaptor sequence (e.g., to amplify the circular DNA by rolling circle amplification or by inverse PCR, etc.), or cleaving the circular DNA by hybridizing an oligonucleotide to the circular DNA to produce a double stranded region, and then cleaving the double stranded region using a restriction enzyme. In an alternative embodiment, recessed oligonucleotide 5 could contain a uracil residue, and the product can be cleaved using a suitable enzyme that excises that residue. In other exemplary embodiments, the circular DNA may be transcribed if sequence 31 comprises the sequence of an RNA polymerase promoter and oligonucleotide 35 hybridizes to that sequence to produce a double stranded RNA polymerase promoter. Other ways of enzymatically processing circular DNA molecule 30 are possible.

As would be recognized by one of skill in the art, there is considerable flexibility in how each of the steps of the method is performed, and, indeed, several of the steps may be done in the same reaction vessel. For example, the cleaving step and the ligating step may be done in single reaction, where the reaction contains both a flap endonuclease that cleaves the flap endonuclease substrate, and a ligase that ligates the cleavage product. In some cases, after the adaptor-ligated DNA is produced, the reaction may be heat inactivated prior to intramolecularly ligating the ends of the adaptor-ligated DNA together to produce the circular DNA. Further, in certain embodiments, an exonuclease may be added to the circular DNA to digest any linear molecules. Also, prior to initiating the initial hybridization step, the genomic DNA does not need to be deliberately fragmented in any way (e.g., by a prior restriction digestion, sonication, or another physical method). However, in certain embodiments (e.g., in embodiments in which the adaptor hybridizes to a target sequence in a genome), the genomic DNA can be fragmented prior to initiating the method.

In certain embodiments, the adaptor used at the beginning of the method may comprise binding sites for a pair of inverse PCR primers. In these embodiments, the enzymatically processing step may comprise (i) amplifying the circular DNA molecule using inverse PCR (using primers that hybridize to the primer binding sites) and (ii) sequencing the amplicon of (i) to obtain at least part of the sequence of genomic sequence 34. The amplifying step of these embodiments may be done using primers that bind to sites provided by the double stranded region 6, or to sites provided by single stranded region 8 (if that sequence is known). In one embodiment, one primer of the pair may hybridize to a site provided by the double stranded region the adaptor 4, and the other primer of the pair may hybridize to a site provided by the single stranded region of the adaptor 4.

Figure 2:
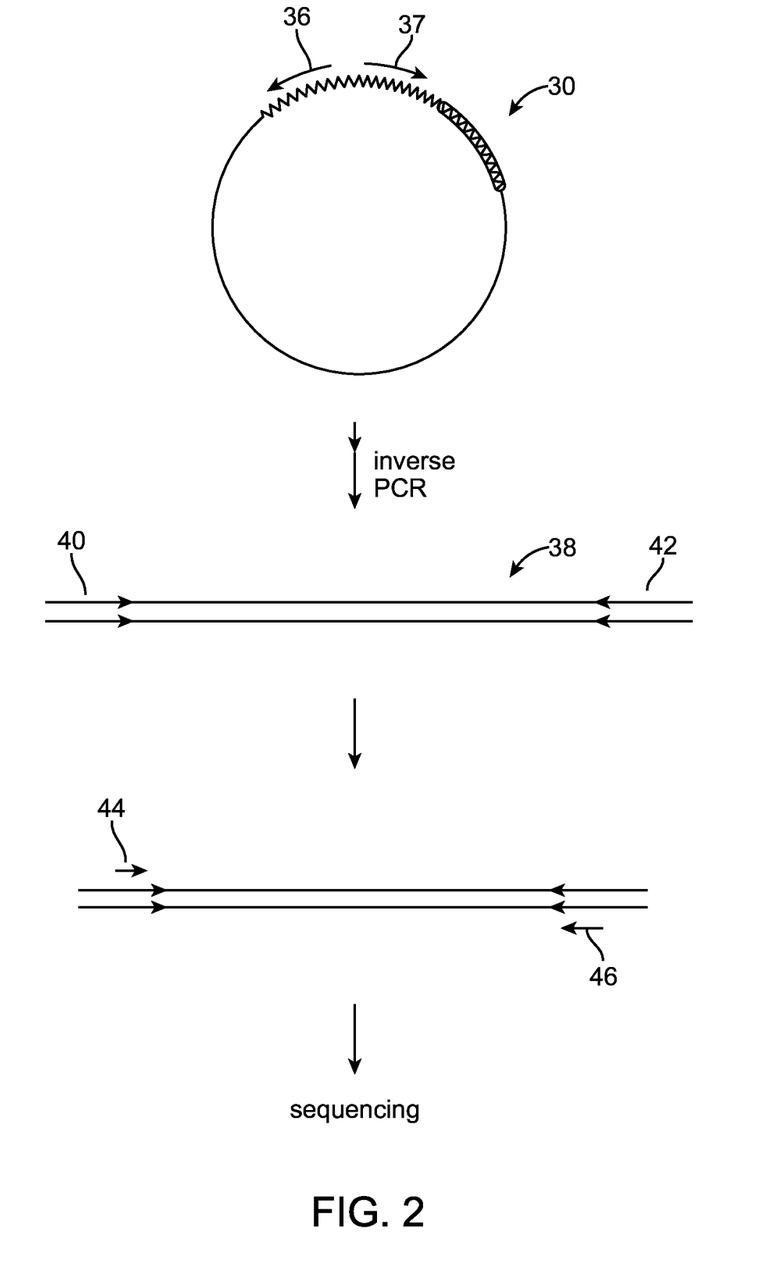
FIG. 2 schematically illustrates one way in which a circular DNA molecule can be sequenced.

One way in which circular DNA molecule can be amplified by PCR is schematically illustrated in FIG. 2. In these embodiments, circular DNA molecule 30 is amplified by PCR using primer pair 36 and 37 to produce amplicon 38 that contains primer sequences 40 and 42 at its ends. This amplicon can be at least partially sequenced using, e.g., primers 44 and/or 46. In certain embodiments, the PCR may be done by clonal PCR (which, as discussed above, is used in many next generation sequencing procedures). In these embodiments, the circular DNA molecules may be applied directly to, e.g., an Illumina substrate, and amplified by inverse PCR using primers that are attached to the substrate. In other embodiments, the inverse PCR may be one using primers that are in solution, and the amplicon produced by inverse PCR may be sequenced (e.g., using a next generation sequencing procedure). In alternative embodiments, the processing step may comprise (i) amplifying the circular DNA molecule using rolling circle amplification to produce a product and (ii) sequencing the product of (i).

As would be apparent, the amplicon produced by inverse PCR may contain sequences that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The sequences may be present in the double stranded region of the adaptor (in which case they are effectively added to genomic sequence 34 by ligation), or they may be present in a 5' tail of inverse PCR primers 36 and 37. In certain cases, the double stranded region of the adaptor may contain two sets of primer binding sites, one for amplifying the circular DNA by inverse PCR, and the other for sequencing the resultant product. The sequence added by the double stranded region may also contain a molecular barcode, positioned downstream of the amplification and sequencing primer binding sites, that can be used to identify from which sample a sequence is derived, or to count how many different starting molecules have been sequenced. In other embodiments, the amplicon may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. Pat Appln Nos. 2006003171 and 20090029477.

As mentioned above, in certain embodiments the single stranded region of the adaptor may comprise a degenerate sequence (e.g., a sequence of N's where N is G, A, T or C) and/or one or more nucleotide analogs, e.g., an inosine, that base pairs with more than one nucleotide (i.e., a combination of G, A, T or C). In particular cases, the single stranded overhang may comprise one or more N's, where N is G, A, T or C, and inosines, where the nucleotides adjacent to the double stranded region are N's and the nucleotides distal to the double stranded region are inosines. In these embodiments, the single stranded region of the adaptor essentially hybridizes anywhere in the genomic DNA, and therefore cleavage occurs at a random position in the genomic DNA. Use of this type of adaptor may result in a library of random fragments of the genome, which finds use in whole genome sequencing applications. In particular cases, the amount of the adaptor hybridized to the genomic DNA may be increased or decreased to obtain shorter or longer fragments of genomic DNA, respectively. Specifically, if more randomly hybridizing adaptor is used, then it should hybridize to more sites in the genome. This should result in shorter fragments. Conversely, if less randomly hybridizing adaptor is used, then it should hybridize to less sites in the genome, which should result in longer fragments. In particular cases, the amount of adaptor may be titrated until a desirable fragment length is obtained. For example, the amount of adaptor can be titrated to produce fragments that have an average size in the range of 100 bases to 10 kb, e.g., 200 bases to 1 kb, as needed.

In other embodiments, the single stranded overhang may comprise a defined sequence that is adjacent to a target locus in genome. In these embodiments, the cleavage and adaptor ligation occurs at a defined position in the genomic DNA. Use of this type of adaptor may result in a library of fragments that contain a target sequence. This embodiment finds particular use in targeted re-sequencing application in which a selected region of a genome (e.g., a region of interest) is isolated and sequenced. In these embodiments, the reaction may be multiplexed in that several adaptors that have the same double stranded region but differing single stranded regions (which hybridize to different sites in the genome under study) may be used. Further, as noted below, this method may be performed on a pool of different samples.

The lengths of the various regions of a subject adaptor may vary greatly depending upon the desired application and how much freight (i.e., how many primer binding sites, barcodes, etc.) are carried by the double stranded region of the adaptor. In certain embodiments, the double stranded region of the adaptor may be of 20-100 base pairs (e.g., 30 bp to 60 bp) in length, and the single stranded region may be of 10-100 bases (e.g., 12-30 bases) in length. As should be readily apparent, the nucleotide sequence of the double stranded region of the adaptor should be designed to that it does not hybridize to the genome under study. In particular embodiments, the recessed oligonucleotide (i.e., the oligonucleotide that is ligated onto a genomic fragment) may comprise an affinity tag, e.g., a biotin moiety, or an optically detectable label such as a fluorescent label. In embodiments in which the recessed oligonucleotide contains an affinity tag, the method may further comprise contacting adaptor-ligated DNA or the circular DNA with a solid support comprising a surface tethered capture agent for the affinity tag, thereby binding molecules that contain the recessed oligonucleotide to the solid support and isolating the those molecules from other nucleic acids in the sample.

The method described above can be employed to manipulate and analyze DNA from virtually any nucleic acid source, including but not limited to genomic DNA and complementary DNA, plasmid DNA, mitochondrial DNA, synthetic DNA, and BAC clones etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the double stranded DNA used in the method may be derived from a mammal, where in certain embodiments the mammal is a human.

In certain embodiments, the double stranded DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

Kits

Also provided by this disclosure are kits for practicing the subject methods, as described above. The subject kits contain at least: a) an adaptor comprising a double stranded region; a single stranded region comprising a 5' overhang; and a nucleotide sequence for subsequent enzymatic processing; wherein the single stranded overhang hybridizes to genomic DNA to produce a substrate for a flap endonuclease; b) the flap endonuclease; c) one or more ligases (e.g., a double stranded ligase such as T4 ligase and/or a single stranded ligase); and d) one or more primers that hybridize to the adaptor, as well as suitable reaction reagents (e.g., buffers etc.) for performing the method. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The invention claimed is:

1. A method comprising:
    a) hybridizing genomic DNA to an adaptor, wherein the adaptor comprises:
        a double stranded region;
        a single stranded region comprising a 5' overhang; and
        a nucleotide sequence for subsequent enzymatic processing;
        wherein the 5' overhang hybridizes to the genomic DNA to produce a substrate for a flap endonuclease, and wherein said 5' overhang consists of a sequence of N nucleotides and/or nucleotide analogs that base pair with any nucleotide, where N is G, A, T or C;
    b) cleaving said substrate using said flap endonuclease to produce a product comprising said adaptor and a flap endonuclease-generated fragment of said genomic DNA that is hybridized to said 5' overhang and ligatable to the recessed end of said double stranded region, wherein said cleaving occurs at a random position in said genomic DNA;
    c) ligating the recessed end of said double stranded region to said fragment to produce an adaptor-ligated DNA;
    d) intramolecularly ligating the ends of said adaptor-ligated DNA to produce a circular DNA molecule; and
    e) enzymatically processing said circular DNA molecule using an oligonucleotide that hybridizes to said adaptor and an enzyme.

2. The method of claim 1, wherein said enzymatically processing comprises primer extension, sequencing, amplification, and/or enzymatic cleavage.

3. The method of claim 1, wherein step e) comprises (i) amplifying said circular DNA molecule by PCR using inverse PCR primers that hybridize to said adaptor to produce an amplicon and (ii) sequencing said amplicon produced by (i).

4. The method of claim 1, wherein step e) comprises (i) amplifying said circular DNA molecule using rolling circle amplification to produce a product and (ii) sequencing said product of (i).

5. The method of claim 3, wherein said amplifying is done using one or more primers that bind to sites in said double stranded region.

6. The method of claim 3, wherein said amplifying is by clonal PCR.

7. The method of claim 3 wherein the products of step (i) are amplified by clonal PCR prior to sequencing.

8. The method of claim 1, wherein said double stranded region comprises a barcode sequence.

9. The method of claim 1, wherein said cleaving step b) and said ligating step c) are done in single reaction.

10. The method of claim 1, wherein said intramolecularly ligating is done using a single stranded ligase.

11. The method of claim 1, wherein said 5' overhang consists of a sequence of N nucleotides.

12. The method of claim 1, wherein said nucleotide analogs are inosine.

13. The method of claim 1, wherein said 5' overhang consists of a sequence of one or more N's, and inosines, where the nucleotides adjacent to the double stranded region are N's and the nucleotides distal to said double stranded region are inosines.

14. The method of claim 1, further comprising titrating the amount of said adaptor hybridized to said genomic DNA to produce fragments that have a desired average size.

15. The method of claim 1, wherein said genomic DNA is human genomic DNA.

16. The method of claim 1, wherein said double stranded region is 20-100 base pairs in length, and said single stranded region is 10-100 base pairs in length.

17. The method of claim 14, wherein the desired average size is between 100 bases and 10 kilobases (kb).

18. The method of claim 14, wherein the desired average size is between 200 bases and 1 kb.

* * * * *